United States Patent
Gribkov

(10) Patent No.: US 9,862,937 B2
(45) Date of Patent: Jan. 9, 2018

(54) PROCESS FOR THE PREPARATION OF HALO-SUBSTITUTED TRIFLUOROACETOPHENONES

(71) Applicant: SYNGENTA PARTICIPATIONS AG, Basel (CH)

(72) Inventor: Denis Gribkov, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/515,303

(22) PCT Filed: Oct. 7, 2015

(86) PCT No.: PCT/EP2015/073119
§ 371 (c)(1),
(2) Date: Mar. 29, 2017

(87) PCT Pub. No.: WO2016/058882
PCT Pub. Date: Apr. 21, 2016

(65) Prior Publication Data
US 2017/0218347 A1 Aug. 3, 2017

(30) Foreign Application Priority Data
Oct. 14, 2014 (EP) .................... 14188743

(51) Int. Cl.
| C07C 45/63 | (2006.01) |
| C07C 45/46 | (2006.01) |
| C07C 201/12 | (2006.01) |
| C12N 9/10 | (2006.01) |
| C12P 19/44 | (2006.01) |

(52) U.S. Cl.
CPC ............ C12N 9/1085 (2013.01); C12P 19/44 (2013.01)

(58) Field of Classification Search
CPC ....... C07C 45/46; C07C 45/63; C07C 201/12; C07C 205/45
USPC ........................................................ 568/316
See application file for complete search history.

(56) References Cited

FOREIGN PATENT DOCUMENTS

| CN | 101177379 A | 5/2008 |
| CN | 101337862 A | 1/2009 |
| CN | 103664511 A | 3/2014 |
| WO | 2012120135 A1 | 9/2012 |

OTHER PUBLICATIONS

Kovalevich et al. Calculation of Equilibrium in Anion-Exchange Extractive Systems. Russian Journal of Applied Chemistry 2007, vol. 80 (10), 1651-1655.*

Ohno et al. Reduction by Model of NAD(P)H. 29. Kinetics and Isotope Effects for the Reduction of Substituted Trifluoroacetophenone. Journal of the American Chemical Society, 1981, vol. 103, 2041-2045.*

International Search Report and Written Opinion for PCT/EP2015/073119, dated Nov. 26, 2015.

Sott et al: "Synthesis of dioxin-like monofluorinated PCBs: for the use as internal standards for PCB analysis", Tetrahedron, Elsevier Science Publishers, Amsterdam, NL, vol. 64, No. 18, Jan. 5, 2008 (Jan. 5, 2008), pp. 4135-4142, XP022551930, ISSN: 0040-4020, DOI: 10. 1016/J. TET. 2008. 01. 003.

Stewart, Ross et al: "The Chromic Acid Oxidation of Aryl Trifluoromethyl Alcohols: Isotope and Substituent Effects", Canadian Journal of Chemistry, vol. 42 , No. 2, Feb. 1, 1964 (Feb. 1, 1964), 439-446, XP055170318, ISSN: 0008-4042. DOI: 10. 1 139(v64-061.

(Continued)

Primary Examiner — Sikarl Witherspoon
(74) Attorney, Agent, or Firm — R. Kody Jones

(57) ABSTRACT

The invention relates to a process for the preparation of a compound of formula I (I), wherein $R_1$ is hydrogen, fluoro or chloro; which process comprises a) reacting a compound of formula II (II), wherein $R_1$ is hydrogen, fluoro or chloro; with a nitration agent to the compound of formula (III), wherein $R_1$ is hydrogen, fluoro or chloro; and b) reacting the compound of formula III with chlorine gas at temperature from 180° C. to 250° C. to the compound of formula I.

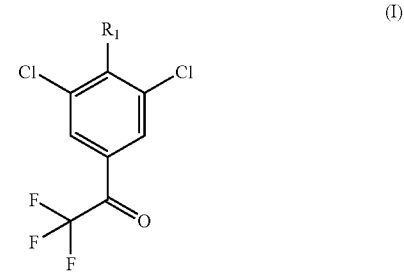

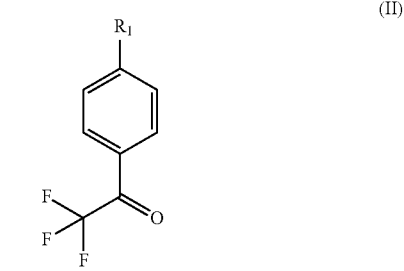

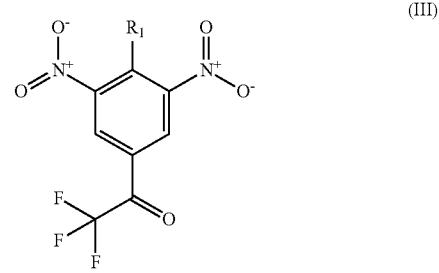

3 Claims, No Drawings

(56) References Cited

OTHER PUBLICATIONS

Extended European Search Report for EP14188743.0, dated Feb. 26, 2015.
Rakhman'Ko E.M. et al.: "Effect of solvating additives on anion-exchange extraction of trichloroacetate anions from aqueous solutions with trinonyloctadecylammonium picrate in toluene", in: Russian Journal of Applied Chemistry, Nauka/Interperiodica, MO, vol. 79, No. I, Jan. 1, 2006 (Jan. 1, 2006), pp. 69-73, XP019299836, ISSN: 1608-3296.

* cited by examiner

PROCESS FOR THE PREPARATION OF HALO-SUBSTITUTED TRIFLUOROACETOPHENONES

RELATED APPLICATION INFORMATION

This application is a 371 of International Application No. PCT/EP2015/073119, filed Oct. 7, 2015, which claims priority to EP Application No.; 14188743.0 filed Oct. 14, 2014, the contents of which are incorporated by reference herein.

The present invention relates to the preparation of halo-substituted 1-aryl-2,2,2-trifluoro-ethanones (compounds Ia, Ib and Ic):

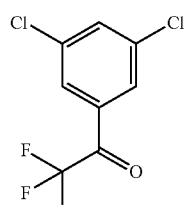

(Ia)

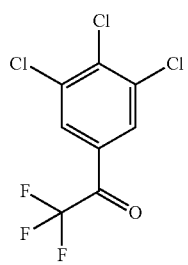

(Ib)

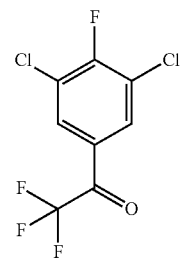

(Ic)

and to intermediates useful for this process. Said compounds are important intermediates for the preparation of pesticidally active isoxazoline-substituted benzamides as for example 1-(3,5-dichloro-4-fluoro-phenyl)-2,2,2-trifluoro-ethanone (Ic) disclosed in EP 1932836A1.

Typically said compounds of formula Ia, Ib and Ic are synthesized by reaction of corresponding organometallic reagents derived from halo-substituted 5-bromo benzenes of formuae IIa, IIb and IIc

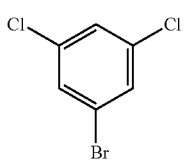

(IIa)

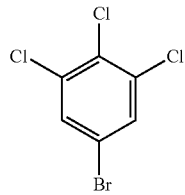

(IIb)

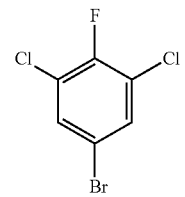

(IIc)

with the derivatives of trifluoroacetic acid (for example ethyl trifluoroacetate). For example, the preparation of 2,2,2-trifluoro-1-(3,4,5-trichlorophenyl)ethanone (I b) is described in WO 2012/120135.

The corresponding bromo derivatives of the formulae IIa, IIb and IIc are not easily available and prepared via multi-step procedures. For example, 5-bromo-1,2,3-trichloro-benzene (II b) can be prepared as described in Narander, N.; Srinivasu, P.; Kulkarni, S. J.; Raghavan, K. V. Synth. Comm. 2000, 30, 3669 and Sott, R.; Hawner, C.; Johansen, J. E. Tetrahedron 2008, 64, 4135.

5-bromo-1,3-dichloro-2-fluoro-benzene (II c) is especially difficult to prepare in particular on a large scale with the only described synthesis being an inefficient multistep approach described in Miller, M. W.; Mylari, B. L.; Howes, H. L.; Figdor, S. K.; Lynch, M. J.; Lynch, J. E.; Koch, R. C. J. Med. Chem. 1980, 23, 1083, CN 101177379, CN 101337862 and CN 103664511 (Scheme 1).

Scheme 1

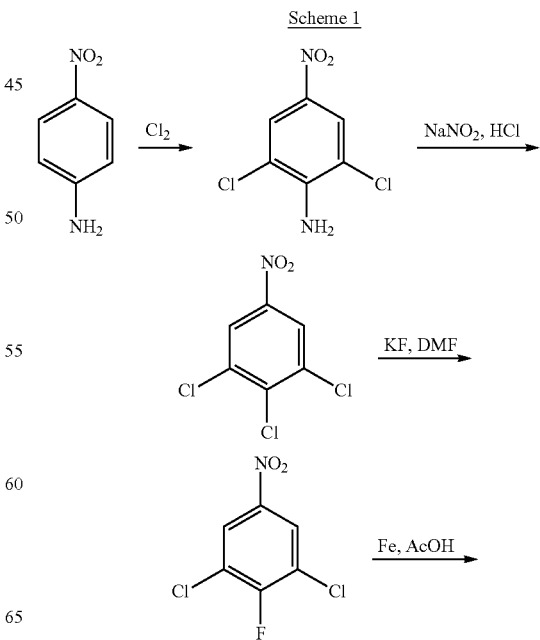

-continued

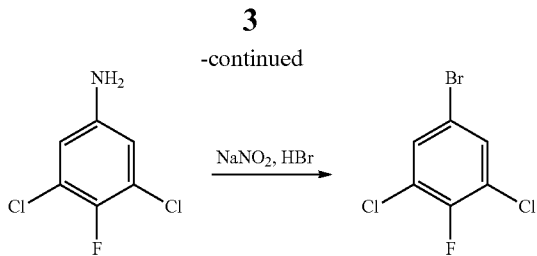

A significant disadvantage of these known processes is the low overall yields caused by the large number of reaction steps (4-6) and consequently high production cost. Moreover the synthesis generates large quantities of waste and has low atom economy.

It is therefore the object of the present invention to provide a process for the preparation of halo-substituted 1-aryl-2,2,2-trifluoro-elhanones with a reduced number of reaction steps, high yield and substantially lower production costs.

Thus, according to the present invention, there is provided a process for the preparation of a compound of formula I

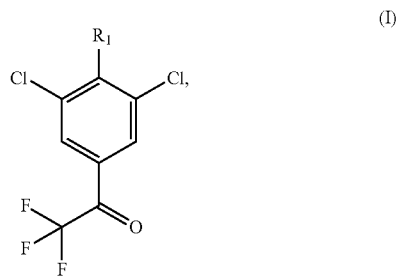

wherein $R_1$ is hydrogen, fluoro or chloro; which process comprises a) reacting a compound of formula II

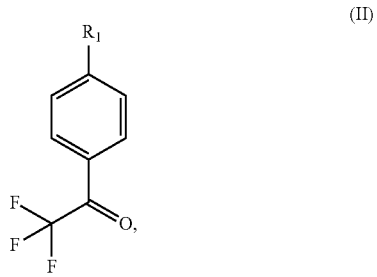

wherein $R_1$ is hydrogen, fluoro or chloro; with a nitration agent to the compound of formula

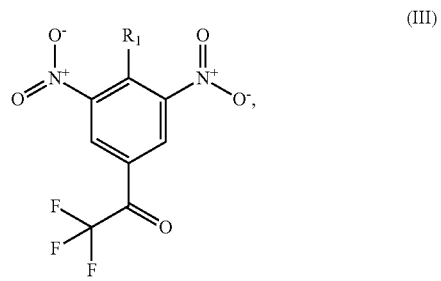

wherein $R_1$ is hydrogen, fluoro or chloro; and b) reacting the compound of formula Ill with chlorine gas at temperature from 180° C. to 250° C. to the compound of formula I.

Reaction step a):

Compounds of formula II are commercially available and several methods are reported in the literature for their preparation. For example, compounds of formula II, wherein $R_1$ is hydrogen or chloro, can be easily synthesized in high yields via Friedel-Crafts acylation of benzene and chlorobenzene respectively with trifluoroacetyl chloride or trifluoroacetic anhydride in the presence of a Lewis acid catalyst (aluminium chloride). However, the preparation of a compound of formula II, wherein $R_1$ is fluoro, via Friedel-Crafts method is only reported in a single publication using expensive 1-(trifluoroacetyl)-4-(dimethylamino)pyridinium trifluoroacetate as an acylating agent. The compound of formula II wherein $R_1$ is fluoro, can be synthesized in analogy to the synthesis of compound of formula II wherein $R_1$ is chloro, using trifluoroacetyl chloride in the presence of aluminium chloride in good yield.

The compound of formula III, wherein $R_1$ is hydrogen, is known (CAS 1960-27-6) and can be prepared via nitration according to Canadian Journal of Chemistry,1964 ,vol. 42, p. 439446; and Journal of the American Chemical Society, 1981, vol.103, # 8 p. 2041-2045.

The compound of formula Ill,

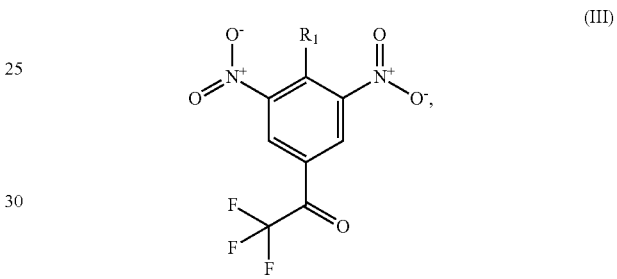

wherein $R_1$ is fluoro, is novel and was developed specifically for the preparation of the compounds of formula I. Accordingly, said compound also form part of the subject matter of the present invention.

The nitration of the compounds of formula II can be performed using nitration agents like a mixture of concentrated sulfuric acid (10-15 equiv. (concentrated or fuming)), and concentrated or fuming nitric acid (2.2-2.5 equiv.) without solvent at temperatures of 100° C.-160° C., preferably 120° C.-140° C. Instead of nitric acid its sodium or potassium salts (sodium nitrate or potassium nitrate) can be also used. Also to minimize the sulfuric acid waste and to improve conversion of starting material and shorten the reaction times, a combination of fuming sulfuric acid (20, 30 or 66% dissolved $SO_3$) and fuming nitric acid (90-100%) is advantageously used. For example, fuming sulfuric acid with 30% $SO_3$ content in combination with 99% fuming nitric acid allows reducing the use rate of sulfuric acid by 50% (5-7 equiv.).

Typically a mixture of di-nitro substituted compounds of formula Ill (major product) and mono-nitro substituted compounds of formula IV

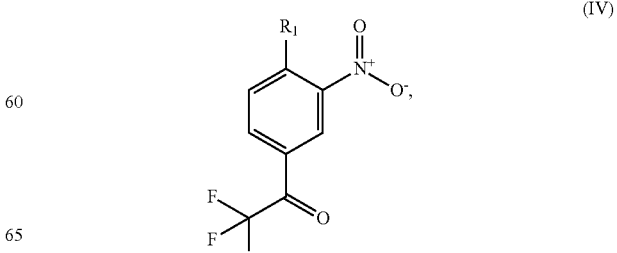

wherein R₁ is hydrogen, fluoro or chloro, is produced. This mixture is easily separable by distillation and the recovered mono-nitro compounds can be subjected to nitration together with compounds of formula II.

This makes the whole process very efficient and high yielding.

Reaction step b):

Substitution of an aromatic nitro group on chlorine atom using chlorine gas at high temperatures (200° C.) is a well-known transformation. However, this transformation is only applicable to a special class of substrates witch can tolerate such drastic conditions. There are no prior art examples known of a substitution on substrates having trifluoroacetyl group in the aromatic ring.

The reaction is performed by passing chlorine gas through a neat compound of formula IV (no solvent) at temperatures ranging preferably from 180° C. to 250° C., more preferably from 200° C. to 220° C. The product can be advantageously removed by distillation during the reaction. This also accelerates conversion of the remaining starting material. A slight vacuum can be applied to facilitate the distillation. If the product cannot be efficiently removed by distillation during the course of the reaction (small scale reactions, not enough material to be continuously distilled), the unreacted starting material of formular III (if there is any left) and the reaction intermediate of formula V (if there is any left)

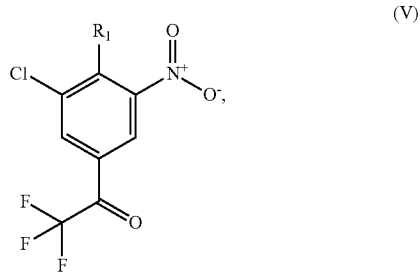

(V)

wherein

R₁ is hydrogen, fluoro or chloro, can be separated from product by fractional distillation afterwards and re-used in the next run.

PREPARATORY EXAMPLES

Example P1

Preparation of the Compound of Formula IIc: 2,2,2-trifluoro-1-(4-fluorophenyl)ethanone

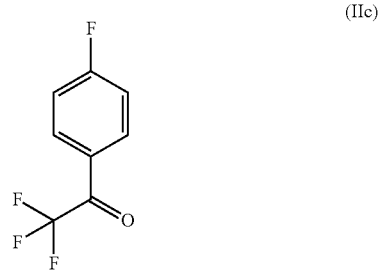

(IIc)

In a 2 L glass reactor equipped with a cooling circulator, a mechanical stirrer and a glass pipe for gas introduction, was placed fluorobenzene (865 g, 9.00 mol). The reactor's content was cooled to −5° C. and finely-powered anhydrous aluminum chloride (444 g, 3.30 mol) was added in one portion. A stream of trifluoroacetyl chloride gas (400 g, 3.02 mol) was introduced under the liquid surface over a period of 3 h at −5° C. (2.2 g /min). Reaction off-gas was scrubbed in a 10% sodium hydroxide solution. The reaction mixture was stirred for additional 3 h at 0° C. and then it was slowly added to ice-cold water (1200 g) while keeping the temperature below 30° C. (intensive cooling required). The aqueous lower layer was separated and the organic layer was washed with water (300 mL). The product was isolated by fractional distillation using 50 cm Vigreux column as follows: Most of fluorobenzene was distilled at normal pressure while increasing the bad temperature from 100 to 140° C. Then the bad temperature was reduced to 80° C. and the apparatus was evacuated to 200 mbar. After distilling remaining fluorobenzene the product was collected at the head temperature of 100-101° C. (200 mbar). Yield 437 g. According to the quantitative ¹H NMR analysis (1,1,2,2-tetrachloroethane as an internal standard) the material had purity of 99%. The recovered fluorobenzene (546 g) was used in the next run.

Als spectroscopic data were in agreement to those of commercially available material.

Example P2

Preparation of the Compound of Formula IIIc:

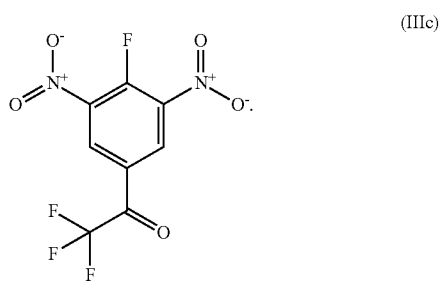

(IIIc)

In a 50 mL 3-neck round-bottom flask equipped with magnetic stirrer, thermometer and dropping funnel was placed fuming sulfuric acid (17.3 g, 20-30% SO₃). The flask content was cooled to 5° C. and compound of formula IIc (10.0 g, 51.5 mmol) was added in one portion. Fuming nitric acid (3.45 g, 54 mmol) was added to the mixture during 10 minutes while keeping the temperature below 15° C. After the addition was completed the reaction mixture was heated to 120° C. in an oil bath. (At this point GC analysis indicated complete conversion of starting material to mono-nitro compound of formula IVc.). Further on a nitrating mixture prepared by a slow addition of fuming nitric acid (4.75 g, 74.7 mmol) to fuming sulfuric acid (24.0 g, 20-30% SO₃) at 0-5° C., was added to the flask during 1 h and 15 min while keeping the temperature at 120-125° C. The reaction mixture was stirred at this temperature for additional 20 h. (At this point GC analysis indicated 54% conversion of mono-nitro intermediate of formula IVc to the di-nitro compound of formula IIIc).

The reaction mixture was cooled to about 50° C. and water (5.0 g) was slowly added. After further cooling to room temperature, the mixture was extracted twice with dichloromethane (20 mL and 10 mL). The combined extract was evaporated to give a mixture of compounds of formula IIIc and IVc (12.36 g).

According to the quantitate $^1$H NMR analysis (1,1,2,2-tetrachloroethane as an internal standard) the mixture contained 57.2% of compound of formula IIIc and I 41.5% of compound of formula IVc.

The mixture was fractionated in vacuum (0.07 mbar) using 12 cm Vigreux column to give 2 pure fractions:

1) compound of formula IVc: b.p. 51-53° C. (0.07 mbar), 4.87 g, slightly yellow liquid, 40% yield
2) compound of formular IIIc: b.p. 95-96° C. (0.07 mbar), 6.63 g, slightly yellow oily liquid, 46% yield According to the quantitative $^1$H NMR analysis (1,1,2,2-tetrachloroethane as an internal standard) and GC analysis both compounds had purity of 99%.

Compound of formula IIIc:
1 H NMR (400 MHz, CDCI3) δ ppm 8.99 (d, $4J_{H-F}$=5.9 Hz, 2H).
13 C NMR (101 MHz, CDCI3) δ ppm 115.8 (q, $1J_{C-F}$=289.8 Hz, 1 C), 126.0 (d, J=5.9 Hz), 131.7, 139.7, 153.0 (d, $1J_{C-F}$=292.7 Hz), 176.2 (d, $2J_{C-F}$=38.3 Hz).
19 F NMR (376 MHz, CDCI3) δ ppm −112.82 (s, 1 F), −71.87 (s, 3 F).

Compound of formula IVc:
$^1$H NMR (400 MHz, CDCI$_3$) δ ppm 7.58 (m, 1H), 8.40 (m, 1 H), 8.79 (m, 1H).
$^{13}$C NMR (101 MHz, CDCI$_3$) δ ppm 116.1 (q, $1J_{C-F}$=290.5 Hz), 120.0 (d, J=22.0 Hz), 126.6 (d, J=4.4 Hz), 128.5, 136.8 (dm, J=10.3 Hz), 137.9, 159.3 (d, $1J_{C-F}$=276.6 Hz), 177.6 (q, $2J_{C-F}$=37.3 Hz).
$^{19}$F NMR (376 MHz, CDCI$_3$) δ ppm −105.15 (s, 1F), −71.88 (s, 3F).

Example P3

Preparation of the Compound of Formula Ic:

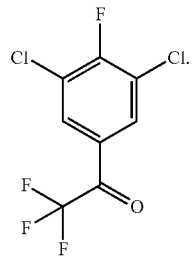

(Ic)

In a 10 mL 2-neck round-bottom flask equipped with magnetic stirrer, glass pipe for gas introduction and reflux condenser was placed compound of formula IIIc (6.00 g, 21.3 mmol, 100% purity). The flask was placed in an oil bath and heated to 220° C. (external temperature). A slow stream of chlorine gas was introduced under the liquid surface over a period of 15 h. Reaction off-gas which contains nitrogen dioxide and excess of chlorine was absorbed in a 10% sodium hydroxide solution. The reaction mixture was cooled to room temperature and discharged (5.01 g). According to the quantitative NMR analysis the crude reaction mixture had the following composition: 30.0% compound of formula Ic, 28.9% compound of formula IIIc (starting material) and 30.9% of the intermediate of formula Vc. This mixture of compounds was fractionated in vacuum (7-9 mbar) using 10 cm Vigreux column to separate the title compound of formula Ic (b.p. 75-78° C., 1.53 g) from the mixture of starting material IIIc and intermediate Vc (3.25 g, distillation residue). The title compound of formula Ic had purity of 91% according to the quantitative $^1$H NMR analysis (1,1,2,2-tetrachloroethane as an internal standard). The distillation residue contained 44.5% of compound of formula IIIc, 46.4% of the intermediate of formula Vc and 1.0% of product of formula Ic. Isolated yield of compound of formula Ic 25%.

Yield of the recovered starting material/intermediate 49%
Compound of formula Ic:
$^1$H NMR (400 MHz, CDCI3) δ ppm 8.05 (dd, $4J_{H-F}$=6.1 Hz, $5J_{H-F}$=0.8 Hz, 2H).
$^{13}$C NMR (101 MHz, CDCI3) δ ppm −116.2 (q, $1_{C-F}$=290.54 Hz), 124.1 (d, J=18.6 Hz), 126.8 (d, J=4.7 Hz), 131.0, 158.7 (d, $1J_{C-F}$=262.7 Hz), 177.6 (q, $2J_{C-F}$=37.08 Hz).
$^{19}$F NMR (376 MHz, CDCI3) δ ppm −102.51 (s, 1F), −71.56 (s, 3F).

Example P4

Preparation of the Compound of Formula IIIb

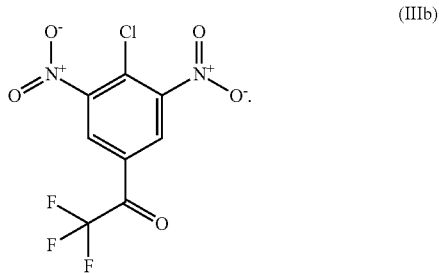

(IIIb)

In a 50 mL 3-neck round-bottom flask equipped with magnetic stirrer, thermometer and dropping funnel was placed fuming sulfuric acid (30.0 g, 20-30% SO$_3$). The flask content was cooled to 5° C. and compound of formula IIb (10.0 g, 47.5 mmol) was added in one portion. Fuming nitric acid (7.00 g, 110 mmol) was added to the mixture during 10 minutes while keeping the temperature below 25° C. After the addition was completed the reaction mixture was heated to 105° C. in an oil bath. It was stirred at this temperature for 2 h and 20 min and then the temperature was increased to 125° C. The reaction mixture was stirred at 125° C. for additional 5 h. (At this point quantitative $^1$H NMR analysis indicated 67% conversion of mono-nitro intermediate of formula IVb to the di-nitro compound of formula IIIb).

The reaction mixture was cooled to room temperature and water (3.6 g) was slowly added. After cooling to room temperature, the mixture was extracted twice with dichloromethane (15 mL and 5 mL). The combined extract was evaporated to give a mixture of compounds of formula IIIb and IVc (12.76 g).

According to the quantitate $^1$H NMR analysis (1,1,2,2-tetrachloroethane as an internal standard) the mixture contained 67.5% of compound of formula IIIb and 27.3% of compound of formula IVb.

The mixture was fractionated in vacuum (0.07 mbar) using 12 cm Vigreux column to give 2 fractions:
1) compound of formula IVc: b.p. 62-64° C. (0.07 mbar), 3.93 g, slightly yellow liquid, 28% yield
2) compound of formular IIIc: b.p. 95-96° C. (0.07 mbar), 7.94 g, yellow oily liquid which rapidly solidified in the receiver (m. p. 60-63° C.), 56% yield.

According to the quantitative $^1$H NMR analysis (1,1,2,2-tetrachloroethane as an internal standard) and GC analysis compound of formula IIIc had purity of 99% and compound of formula IVc of 87%

Compound of formula IIIb:

1 H NMR (400 MHz, CDCl3) δ ppm 8.62 (s, 2H).

13 C NMR (101 MHz, CDCl3) δ ppm 115.8 (q, 1J$_{C-F}$=289.8 Hz), 127.7, 128.1, 129.4, 150.2, 176.5 (d, 2J$_{C-F}$=38.1 Hz).

19F NMR (376 MHz, CDCl3) δ ppm −71.96.

Compound of formula IVb:

$^1$H NMR (400 MHz, CDCl$_3$) δ ppm 7.82 (d, J=8.5 Hz, 1H), 8.21 (dm, J=8.6 Hz, 1H), 8.55 (d, J=1.8 Hz, 1 H).

$^{13}$C NMR (101 MHz, CDCl$_3$) δ ppm 116.1 (q, 1J$_{C-F}$=290.5 Hz), 126.9 (d, J=2.2 Hz), 129.1, 133.1, 133.5 (q, J=2.20 Hz), 134.6, 148.4, 177.9 (q, 2J$_{C-F}$=36.6 Hz).

$^{19}$F NMR (376 MHz, CDCl$_3$) δ ppm −71.92.

Example P5

Preparation of the Compound of Formula Ib

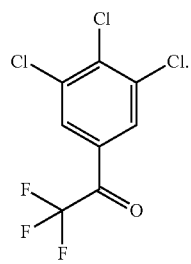

In a 25 mL 2-neck round-bottom flask equipped with magnetic stirrer, glass pipe for gas introduction and reflux condenser was placed compound of formula IIIb (7.67 g, 18.8 mmol, 99% purity). The flask was placed in an oil bath and heated to 220° C. (external temperature). A slow stream of chlorine gas was introduced under the liquid surface over a period of 20 h. Reaction off-gas which contains nitrogen dioxide and excess of chlorine was absorbed in a 10% sodium hydroxide solution. After this time the conversion of starting material was 99.6% (GC area %, FID). The reaction mixture was purged with nitrogen to remove chlorine gas from the system and simultaneously cooled to about 60° C. Dichloromethane (10 mL) was introduced through the reflux condenser and the resulting solution was discharged. The flask was rinsed with a small quantity of dichloromethane (5 mL). The solvent was removed by rotary evaporation to afford compound of formula Ib as white crystalline material (6.62 g, m. p. 54-56° C.). The title compound of formula Ic had chemical purity of 99% according to the quantitative $^1$H NMR analysis (1,1,2,2-tetrachloroethane as an internal standard). Yield 93%

$^1$H NMR (400 MHz, CDCl$_3$) δ ppm 8.05 (d, J=0.8 Hz, 2H).

$^{13}$C NMR (101 MHz, CDCl$_3$) δ ppm 116.1 (q, 1J$_{C-F}$=290.5 Hz), 129.0, 129.5 (m), 135.8, 139.5, 177.9 (q, 2J$_{C-F}$=36.6 Hz).

$^{19}$F NMR (376 MHz, CDCl$_3$) δ ppm −71.65.

The invention claimed is:

1. A process for the preparation of a compound of formula I

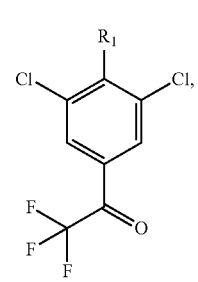

wherein R$_1$ is hydrogen, fluoro or chloro; which process comprises a) reacting a compound of formula II

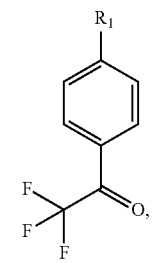

wherein R$_1$ is hydrogen, fluoro or chloro; with a nitration agent to the compound of formula

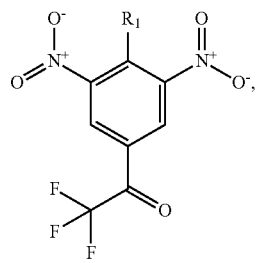

wherein R$_1$ is hydrogen, fluoro or chloro; and b) reacting the compound of formula III with chlorine gas at temperature from 180° C. to 250° C. to form the compound of formula I.

2. A process according to claim 1, characterised in that the nitration agent is selected from sulfuric acid, nitric acid and their salts.

3. The compound of formula III,

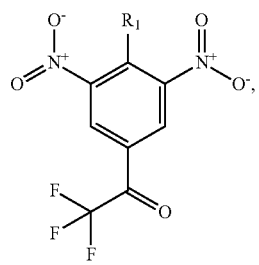

wherein R$_1$ is fluoro.

* * * * *